United States Patent [19]

Bremer et al.

[11] Patent Number: 5,124,291
[45] Date of Patent: Jun. 23, 1992

[54] METHOD FOR DEAGGLOMERATING AND RE-EXPOSING CATALYST IN A FLUID BED REACTOR

[75] Inventors: Noel J. Bremer, Kent; Louis R. Trott, Solon; Timothy R. McDonel, Brecksville, all of Ohio

[73] Assignee: The Standard Oil Company, Cleveland, Ohio

[21] Appl. No.: 614,311

[22] Filed: Nov. 15, 1990

[51] Int. Cl.$^5$ .................... B01J 38/72; B01J 38/04; C07D 307/34; C07C 253/00
[52] U.S. Cl. ..................... 502/21; 208/113; 209/138; 423/507; 502/20; 502/30; 502/34; 502/518; 549/256; 549/257; 549/258; 549/259; 549/260; 558/320
[58] Field of Search ............. 502/21, 20, 515–518, 502/30, 34, 41; 549/256–260; 558/320; 209/138

[56] References Cited

U.S. PATENT DOCUMENTS

| 2,605,234 | 7/1952 | Friedman | 502/21 |
| 2,651,600 | 9/1953 | Taff et al. | 502/21 |
| 2,958,650 | 11/1960 | Dart et al. | 502/21 |

Primary Examiner—Paul E. Konopka
Attorney, Agent, or Firm—D. P. Yusko; M. F. Esposito; L. W. Evans

[57] ABSTRACT

A fluid bed catalyst which has lost activity or fluidization quality through agglomeration, contamination, or a physical or chemical change on the surface of the catalyst is deagglomerated and/or its surface re-exposed, by contacting the fluidized catalyst with a high velocity gas sufficient to cause multiple collisions among the catalyst particles and thereby deagglomerating the particles and/or abrading the surface of the particles to expose fresh catalyst.

8 Claims, 1 Drawing Sheet

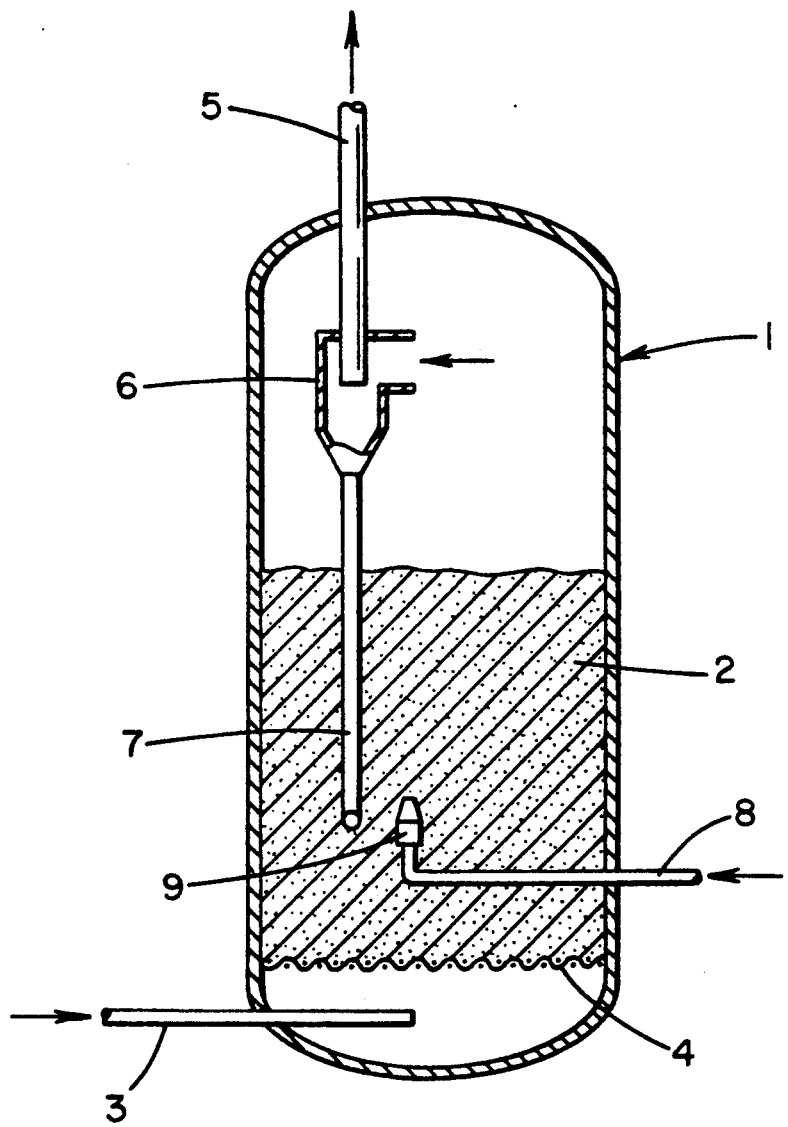
FIGURE

METHOD FOR DEAGGLOMERATING AND RE-EXPOSING CATALYST IN A FLUID BED REACTOR

BACKGROUND OF THE INVENTION

1. Field of the Invention

This invention relates to a method for enhancing the performance of a fluid bed catalyst which has lost activity or fluidization quality due to contaminants or other physical or chemical change on the surface of the catalyst. More specifically, the invention relates to a method for abrading the catalyst surface while in use to remove a thin layer of the catalyst surface thereby exposing fresh catalyst. Additionally, the invention relates to a method for deagglomerating catalyst particles.

2. Description of the Art

In a fluid bed catalytic reactor, finely divided solid particles of catalyst are contacted with a typically vaporous reaction medium. The catalyst particles are lifted and agitated by a rising stream of process gas such that they appear suspended in the gas stream and may resemble a boiling liquid, hence the term "fluid bed".

The most well-known and one of the early applications of fluid bed reactor technology is catalytic cracking of oils to produce gasoline and other light hydrocarbons. Other uses include coking of residua; coke gasification; catalytic oxidation of benzene or butane to maleic anhydride; ammoxidation of propylene to acrylonitrile; and hydrogen chloride oxidation to chlorine.

The instant invention focuses on the catalysts used in fluid bed reactors. Through use and over time, some fluid bed catalysts lose activity as the surface of the catalyst is fouled by contaminants or by-products generated by the reaction or as the surface of the catalyst undergoes a physical or chemical transition to a less catalytic form. Additionally, as contaminants or a physical or chemical change occur on the surface of the catalyst, some catalysts become "sticky" and the small fluid bed particles begin to agglomerate into larger particles. The agglomerated particles result in a decrease of catalytic surface area, thereby affecting the overall performance of the fluid bed catalyst. Further, the agglomerated particles impede the natural circulation and fluidization of the catalyst bed.

Typically, the solution to the above problems is to replace all or part of catalyst in the fluid bed reactor. This is very costly in terms of the cost of catalyst but also in the cost of lost production which could result from shutting down the fluid bed reactor to accommodate a catalyst changeout.

An object of the invention described herein is a method designed to cure the problems brought upon by agglomeration, contamination or a physical or chemical change on the catalyst surface and to prolong catalyst life.

SUMMARY OF THE INVENTION

A method has been discovered for deagglomerating a fluid bed catalyst and re-exposing the surface of a fluid bed catalyst which has lost activity or fluidization quality through contamination or a physical or chemical change on the surface of the catalyst. The method is intended to be practiced inside an operating fluid bed reactor, but optionally may be practiced exterior to the reactor in a continuous or discontinuous fashion.

In a preferred embodiment, the method comprises equipping a fluid bed reactor with at least one jetting nozzle to which a gas is supplied from a source external to the reactor. The jetting nozzle is positioned inside the reactor such that the nozzle is immersed in the catalyst bed and such that gas exiting the nozzle comes into immediate contact with the catalyst. The gas exits the nozzle at an escape velocity sufficient to contact the fluidized fluid bed catalyst particles and cause numerous collisions among the catalyst particles. The impact of the multiple collisions of catalyst particles abrades the surface of the catalyst, thereby removing any contamination or less catalytic material on the surface of the catalyst and exposing fresh catalyst.

DETAILED DESCRIPTION OF THE DRAWINGS

The FIGURE is a simplified cross-section of a fluid bed reactor illustrating an embodiment of the instant invention.

DETAILED DESCRIPTION OF THE INVENTION

A fluid bed reactor is any reaction vessel in which a gas-solid or liquid-solid contacting process occurs. In the reactor, a bed of finely divided solid particles (i.e. the fluid bed catalyst) is lifted and separated by using a stream of process gas or liquid. Fluid bed reactors exist in all shapes and sizes. Typically the reactors are equipped with a grid near the bottom of the reactor which supports the catalyst bed while allowing process feed to pass through. The remainder of this description focuses in the practice of the instant invention in gas-solid contacting processes. However, the methods described herein are equally applicable to liquid-solid contacting processes.

In a gas-solid contacting process, the process product gas exits at the top of the reactor. Since the product gas typically carries catalyst particles with it, the product gas flows through a separator to remove the catalyst particles which are returned via a dipleg to the catalyst bed. The separator may be any solid recovery device, examples are cyclones and filters.

Fluid bed catalysts are finely divided solid particles which vary in size, weight, shape and composition depending on the application. Macroscopically, fluid bed catalyst most often resemble a powder. However, macroscopically such catalysts may also appear as small beads. Fluid bed catalyst particles typically range in size from 10 to 200 microns.

In some applications, the effectiveness of the fluid bed catalyst is lost due to the formation of contaminants or a physical or chemical change on the surface of the catalyst. This condition may cause a decrease in catalyst activity or may cause the catalyst to become "sticky" in which case the catalyst particles tend to agglomerate thereby losing both fluidization quality and/or catalyst activity.

In the practice of the instant invention, the fluid bed reactor is equipped internally with one or more jetting nozzles through which a high velocity gas is fed into the catalyst bed. During the practice of the instant invention the catalyst is maintained under fluidization conditions (i.e. fluidized) caused by a rising stream of process or other gas lifting, agitating and suspending the catalyst particles in the rising gas. The force of the gas stream causes numerous collisions among the fluidized catalyst particles and the impact caused by the collision of catalyst particles abrades the catalyst surface and removes any contaminants on the surface to reveal fresh catalyst. Additionally, the impact caused by the collision of the catalyst particles will deagglomerate (i.e. break apart) any agglomerated catalyst particles. The invention may also be practiced in any vessel equipped with any means (such as a nozzle or a gas distribution grid or plate containing one or more holes) to accomplish the contacting of a stream of high velocity gas with the fluidized catalyst particles.

Preferably the invention is practiced in a fluid bed reactor equipped with more than one nozzle. The nozzles, used herein, may be of any shape or size and provide any "spray" pattern. The nozzles may be as simple as an open-ended pipe or may be a short tube ending with a taper or a constriction to accelerate or direct the flow of the gas exiting the tube. Orifice size is not critical to the practice of the invention. Orifices as small as 0.016 inches in diameter (in a gas distribution grid containing a triad of 0.016 inch diameter setting holes) have been employed. Typical orifice sizes are 0.0625 inches to 0.250 inches in diameter. More typical are orifice sizes between 0.125 inches and 0.1875 inches in diameter. Nozzle orifice sizes of 9/64" and 5/32" in diameter are preferred. The escape velocity of the gas must be sufficient to propel the catalyst particles into numerous collisions with enough force to abrade the surface of the catalyst. Typically, a harder catalyst will require a greater escape velocity. Escape velocities up to the speed of sound may be employed. The nozzle orifice and gas flow rate are sized for the gas velocity to be utilized. Preferred gas velocities are in the range of 200 to 1200 fps. More preferred are gas velocities between 600 and 1100 fps. Preferably, the gas velocity is such that the gas-catalyst "contact zone" extends several inches in front of the nozzle into the catalyst bed. The nozzle may be directed to provide a stream of high velocity gas cocurrent, countercurrent or crosscurrent to the fluidizing process gas. Preferably the nozzle is directed to provide a stream of high velocity gas cocurrent with the fluidizing process gas.

The nozzle or nozzles may be located anywhere within the catalyst bed, where the jetting gas will be able to contact the fluidized catalyst particles. For example, the nozzles may be placed just inside the reactor wall or the nozzles may be centered in the reactor. In order to maximize the effectiveness of the instant invention, the nozzles should be located inside the reactor, where the circulation of catalyst is the greatest. This maximizes the amount of total catalyst charge which comes into contact with the gas. For this reason, the jetting nozzles are preferrably located adjacent to or in the proximity of the dipleg opening (i.e., the point of entry for catalyst being returned to the reactor from the separator). Care should be taken to insure that the gas exiting from a nozzle does not propel the catalyst into any internal component of the reactor, since a collision between catalyst and reactor component will more than likely pulverize the catalyst and the repeated collisions will damage the reactor component.

The high velocity gas may be any gas or vaporized liquid which is inert or beneficial to the process. Typically, this gas is supplied to the nozzle from a source external to the reactor. Where the fluid bed reactor is used in an oxidation reaction, air is typically used. However, an inert gas such as nitrogen or the reaction feed gas may also be used. In the practice of this invention in operating (i.e., in production) commercial scale reactors, the incremental increase of the total gas throughout is negligible.

The process for deagglomerating the catalyst and/or re-exposing the catalyst surface can be practiced intermittently or continuously, depending upon the needs of the catalyst and nozzle parameters such as number of nozzles, the location of nozzles and the escape velocity of the gas leaving the nozzle.

The contamination or the less catalytic material on the surface of the catalyst which is abraded from the catalyst is typically removed from the reactor with the reactor effluent and then separated from the reaction production by any suitable separation methods (e.g. cyclonic devices, filters, etc.). A key to the practice of the instant invention is the control of the gas velocity and placement of the nozzles to maximize the beneficial effects of re-exposing the catalyst surface and/or deagglomerating the catalyst while on the other hand minimizing the amount of abrading to the catalyst surface in order to minimize the loss of catalyst.

An embodiment of instant invention is illustrated in the FIGURE. Inside a fluid bed reactor 1 is a bed of fluid bed catalyst 2. The process feed gas enters the reactor via line 3 and passes through the gas distribution grid 4 into the catalyst bed. The vaporous reactor product containing entrained catalyst particles enters the cyclone 6, where the reaction product and catalyst are separated. The vaporous reaction product exits the reactor via line 5. The catalyst is returned to the catalyst bed$^2$ via the dipleg 7. High velocity gas is fed into the reactor via line 8 and is directed into the catalyst bed through nozzle 9.

The instant invention has utility in any catalytic fluid bed process where the catalyst surface becomes contaminated by reaction by-products or a physical or chemical change in the catalyst composition. In such situations the catalyst will lose activity and/or fluidization quality. By abrading the surface of the catalyst to expose fresh catalyst or to deagglomerate catalyst, activity and/or fluidization quality is restored and catalyst life is prolonged. Representative processes in which the instant invention may be employed are the catalytic cracking of oils to produce gasoline and other light hydrocarbons, the coking of residua, coke gasification, the oxidation of benzene or n-butane or maleic anhydride, the ammoxidation of propylene to acrylonitrile, and the oxidation of hydrogen chloride to chlorine.

As described herein, the high velocity gas is contacted with the fluidized catalyst inside the reactor while in operation. The instant invention may also be practiced by locating the nozzles inside the dipleg. Further, fluid bed reactors equipped with a regenerator which removes catalyst to be treated or reactivated and then returned to the reactor, the catalyst surface may be re-exposed and/or the catalyst deagglomerated as described herein inside the regenerator or the catalyst transfer lines between the reactor and the regenerator. Lastly, the instant invention may also be practiced by removing the catalyst from the reactor, re-exposing the catalyst surface and/or deagglomerating the catalyst as described herein and then returning the catalyst to the reactor.

The foregoing description is not intended to be exhaustive or to limit the invention to the precise form disclosed, and obviously many modifications and variations are possible in light of the above disclosure. The purpose of this description is to explain the principle of the invention and its practical applications and to thereby enable others skilled in the art to utilize the invention in its various embodiments and with various modifications as are suited to the particular use contemplated. It is intended that the invention be defined only by the following claims.

The claimed invention is:

1. A method for at least one of deagglomerating fluid bed catalyst particles or re-exposing the surface of fluid bed catalyst particles, whose surface has become contaminated or has undergone a physical or chemical change during use in the production of acrylonitrile or maleic anhydride, the method comprising contacting the fluid bed catalyst particles under fluidization conditions with a gas having a velocity between about 200 and 1200 feet per second and sufficient to cause numerous collisions among the catalyst particles with sufficient impact to at least one of deagglomerate the fluid bed catalyst particles or abrade the surfaces of the catalyst particles to remove the contaminated or changed surfaces.

2. The method of claim 1, wherein the gas is air or nitrogen.

3. The method of claim 1, wherein the method is conducted in any vessel equipped with a means to contact a stream of the gas with the fluidized catalyst.

4. A method for at least one of deagglomerating fluid bed catalyst particles or re-exposing the surfaces of fluid bed catalyst particles, whose surfaces have become contaminated or have undergone a physical or chemical change during use in the production of acrylonitrile or maleic anhydride, the method comprising (a) maintaining the catalyst particles in a fluid bed reactor under fluidization conditions wherein the fluid bed reactor is equipped with at least one jetting nozzle to which a gas is supplied from a source external to the reactor and which is positioned inside the reactor such that the nozzle is immersed in the catalyst particles and that gas exiting the nozzle comes into immediate contact with the catalyst particles; and (b) passing through the nozzle a gas at an escape velocity of about 200 to about 1200 feet per second from the nozzle wherein the gas causes numerous collisions among the catalyst particles with sufficient impact to at least one of deagglomerate the fluid bed catalyst particles or abrade the surfaces of the catalyst particles and remove the contaminated or changed surfaces.

5. The method of claim 4 wherein the gas is air or nitrogen.

6. The method of claim 4, wherein the fluid bed reactor is equipped with a cyclone to separate catalyst from a stream of gaseous effluent and wherein the cyclone is equipped with a dipleg to return catalyst to the reactor and wherein the nozzle is located in the proximity of the exit for catalyst from the dipleg.

7. The method of claim 4, wherein the method for re-exposing the catalyst surface is being conducted while the fluid bed reactor is in operation producing maleic anhydride or acrylonitrile.

8. The method of claim 4, wherein the nozzle orifice opening is between 0.125 inches and 0.1875 inches in diameter.

* * * * *